United States Patent [19]

Salera

[11] 4,166,451
[45] Sep. 4, 1979

[54] HEAT SENSING INSTRUMENT PROBE

[76] Inventor: Edmond A. Salera, 714 Surf View Dr., Santa Barbara, Calif. 93109

[21] Appl. No.: 827,845

[22] Filed: Aug. 26, 1977

[51] Int. Cl.² ............................ A61B 5/00; G01K 7/22
[52] U.S. Cl. ................................. 128/736; 73/362 AR; 338/22 R; 338/28
[58] Field of Search .................. 128/2 H; 73/362 AR; 338/28, 22 R

[56] References Cited

U.S. PATENT DOCUMENTS

| | | | |
|---|---|---|---|
| 2,740,031 | 3/1956 | Addink | 338/28 |
| 2,753,247 | 7/1956 | Greanias et al. | 338/28 |
| 2,961,625 | 11/1960 | Sion | 338/28 |
| 3,147,457 | 9/1964 | Gill et al. | 338/28 |
| 3,593,704 | 7/1971 | Schwab | 128/2 H X |
| 3,738,173 | 6/1973 | Sato | 338/28 X |
| 3,822,598 | 7/1974 | Brothers et al. | 73/362 AR |
| 3,872,727 | 3/1975 | Johnson | 73/262 AR |
| 3,919,680 | 11/1975 | Veno et al. | 338/28 |
| 3,933,149 | 1/1976 | Salera et al. | 128/2 H |

*Primary Examiner*—Lee S. Cohen
*Attorney, Agent, or Firm*—William W. Haefliger

[57] ABSTRACT

Local body heat source sensing instrumentation comprises
(a) a probe including a heat conductive, metallic tip having an outer surface shaped for application in heat transfer proximity with a patient's body,
(b) non-metallic material at the inner side of said tip, said material characterized as electrically insulative and heat conductive, and
(c) an electrically energizable element embedded in said material at a location to detect heat transfer between said surface and source, via said tip and said material.

8 Claims, 9 Drawing Figures

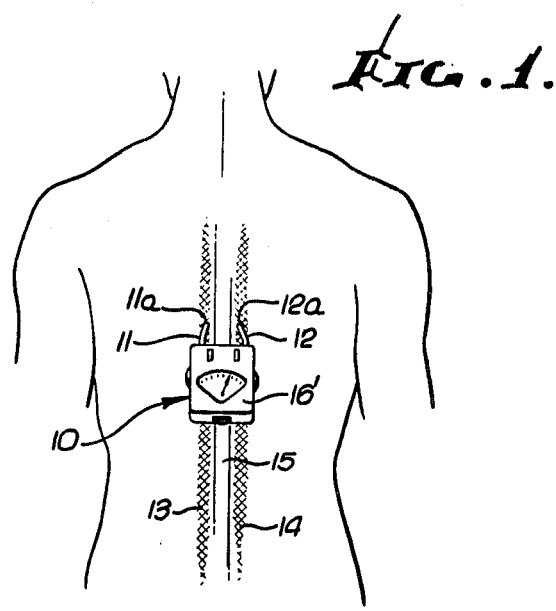
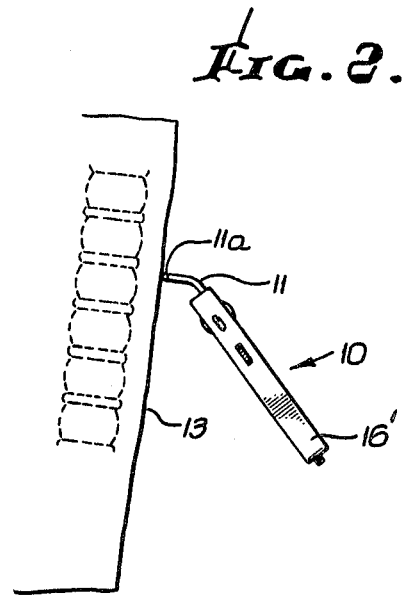
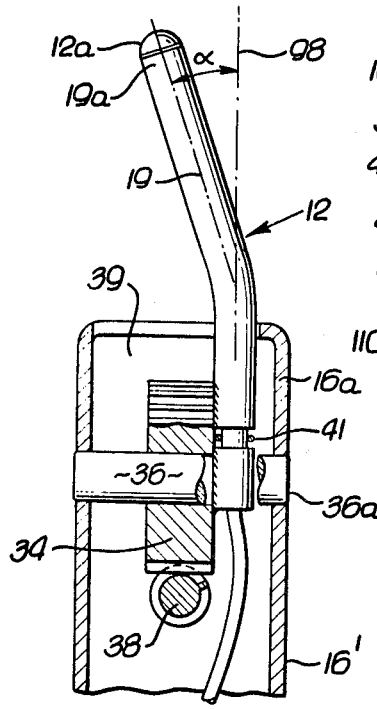
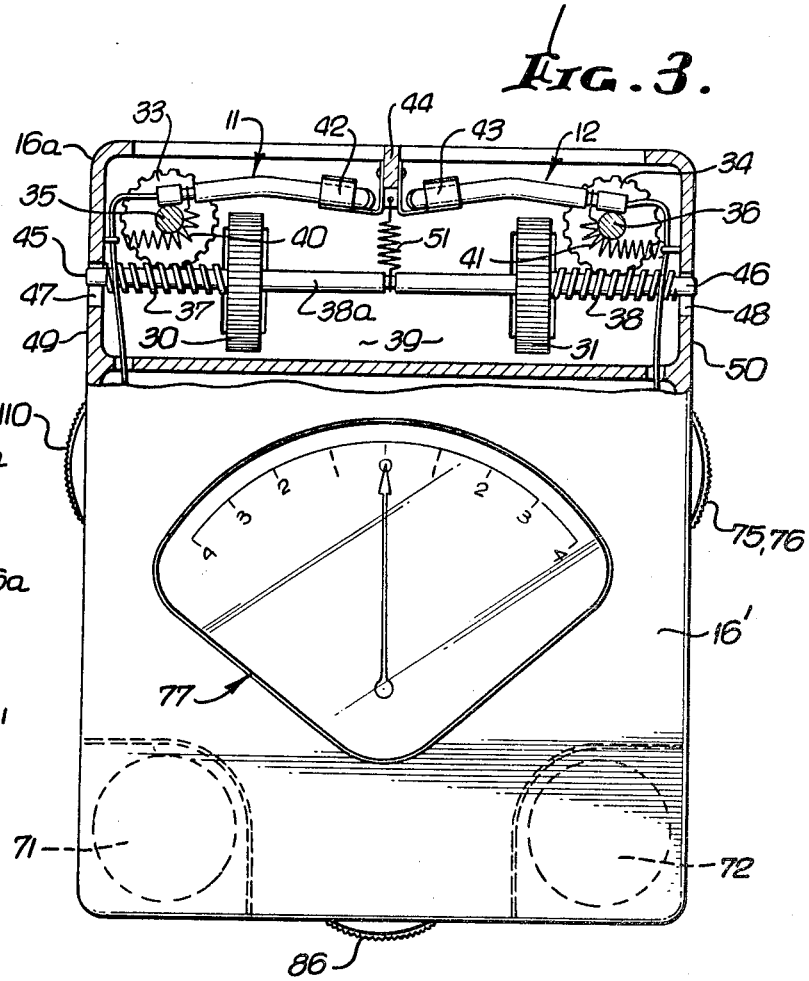

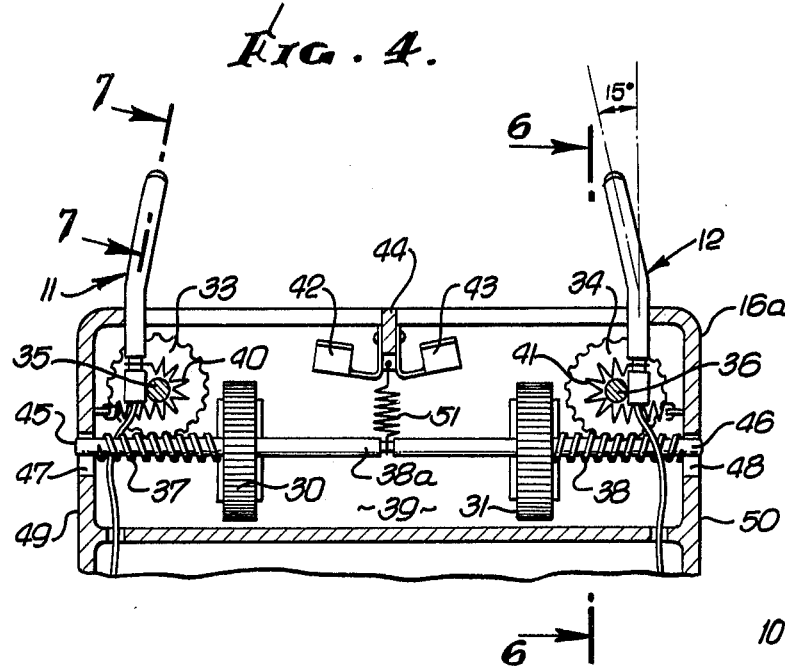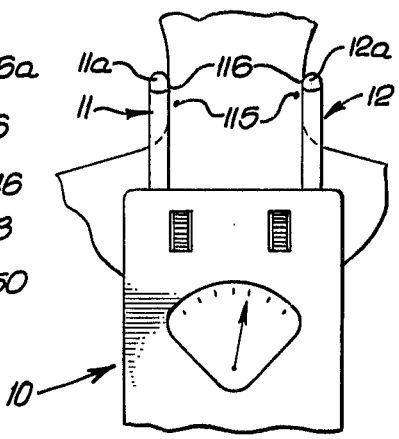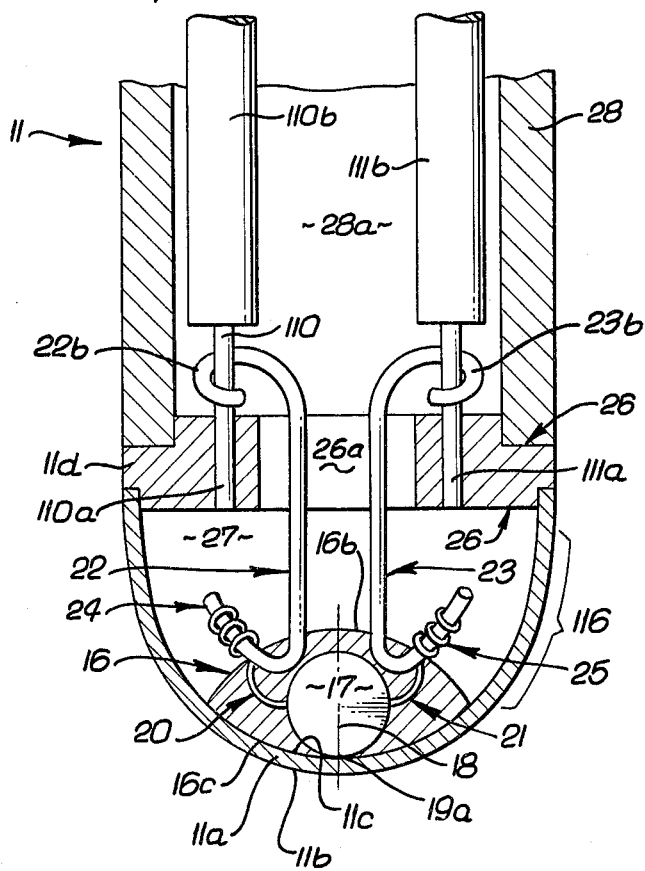

HEAT SENSING INSTRUMENT PROBE

BACKGROUND OF THE INVENTION

This invention relates generally to instrumentation for sensing local areas or zones of patient body heat, and more particularly concerns such instrumentation effective to sense differential heating of local body areas, as for example skin areas proximate the spinal column.

There is a need for an easily usable, accurate, pocket-sized device that will operate to detect differential heating of patient skin zones. In this regad, it is found that the temperaures of such zones proximate sub-surfaces tissue or muscles in spasm, or sites of bruising or injury are slightly higher than the temperatures of uninjuried tissued zones. In particular, there is need for such a device which may be rapidly applied along the spinal column of a patient to isolate zones along the vertebra which may be in spasm, so that such areas may be investigated.

A device satisfying much of the above need is disclosed on my U.S. Pat. No. 3,933,149; however, certain problems remain. That prior device incorporated a sensor constructed to prevent sensed heat from shorting around the heat sensitive thermistor and into the supporting metal tube. For this purpose, semi-heat conductive epoxy was provided to both support and protect the thermistor, and also to attach to the metal tube; however, this undesirably reduced the sensitivity of the probe, especially when the side of the probe tip touched the skin area during scanning, as for example the patient's neck region.

SUMMARY OF THE INVENTION

It is a major object of the invention to provide instrumentation fulfilling the above need, and also providing a highly sensitive improved probe, with advantages in construction and operation, as will appear. Basically, the instrument comprises:

(a) a probe including a heat conductive, metallic tip having an outer surface shaped for application in heat transfer proximity with a patient's body, (b) non-metallic material at the inner side of said tip, said material characterized as electrically insulative and heat conductive, and (c) electrically energizable means embedded in said material at a location to detect heat transfer between said surface and source, via said tip and said material.

As will appear, the tip is metallic and typically has the shape of a shell with a convex outer surface; the electrically energizable means comprises a thermistor bead embedded in epoxide resin localized near the shell end; and a heat insulative header mounts the shell and attaches to the metal tube in spaced relation to the epoxide resin in which the bead is embedded. This leaves shell area at the side of the tip free for contact with skin areas to produce good heat coupling to the thermistor bead. Further, the metal tip then has good heat sensitivity over its entire area. The bead is glass covered.

As will also appear, a second probe may also be provided on a carrier, the probes located, when extended, to straddle the patient's neck region; and actuator means is typically provided on the carrier to deploy and retract the probes.

These and other objects and advantages of the invention as well as the details of an illustrative embodiment, will be more fully understood from the following description and drawings, in which:

DRAWING DESCRIPTION

FIG. 1 is an elevation showing use of instrumentation embodying the invention;

FIG. 2 is an enlarged side elevation showing use of the FIG. 1 instrumentation;

FIG. 3 is an enlarged frontal view of the FIG. 1 instrumentation, partly broken away to show interior details;

FIG. 4 is a fragmentary view of a portion of the FIG. 3 instrument, showing probes in extended, active positions;

FIG. 5 is a side elevation of the instrument, with probes extended as in FIG. 4;

FIG. 6 is an enlarged section on lines 6—6 of FIG. 4;

FIG. 7 is an enlarged section lines 7—7 of FIG. 4;

FIG. 8 is a view like FIG. 1, showing neck scanning; and

DETAILED DESCRIPTION

Figure 9:
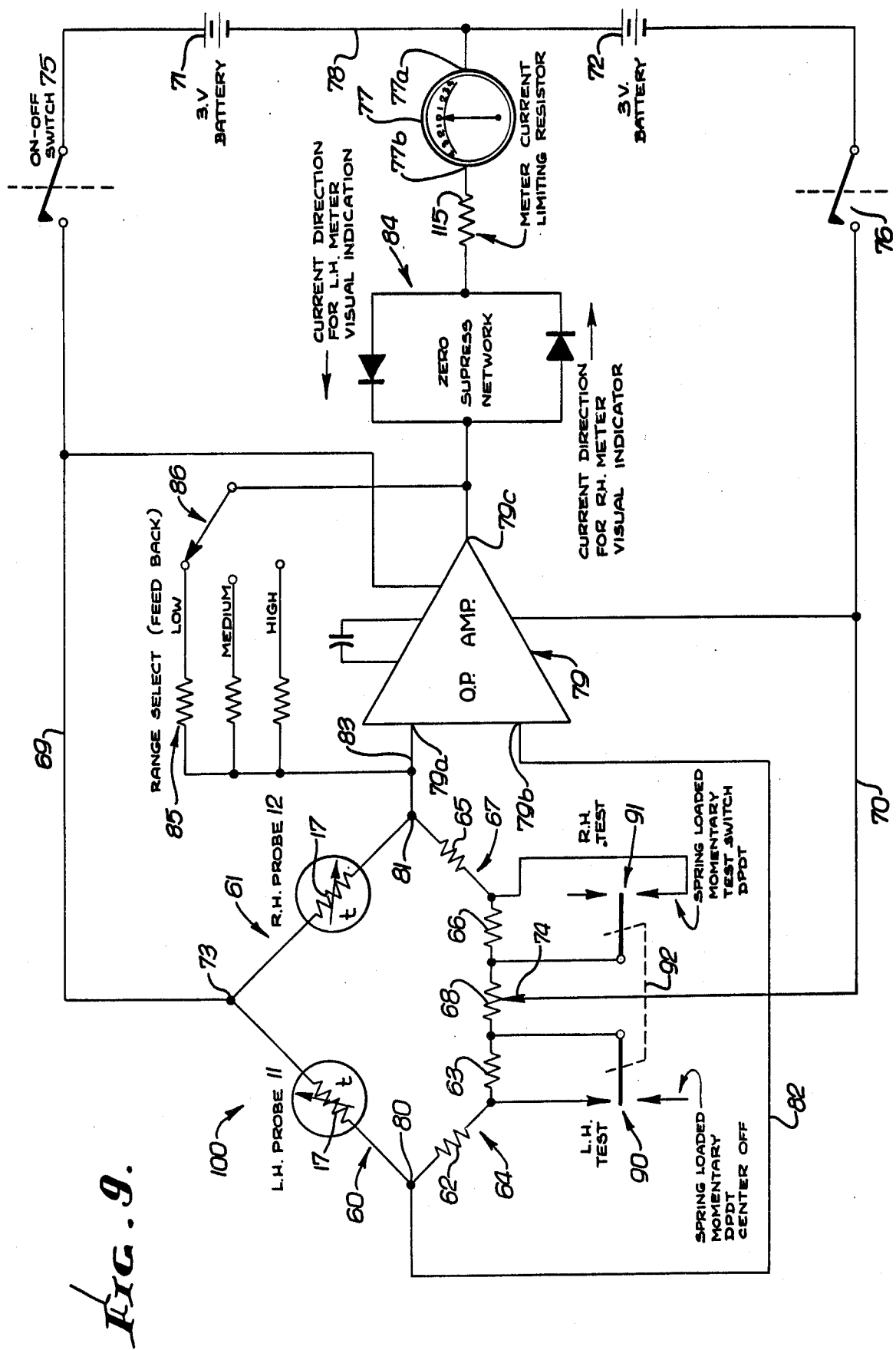
FIG. 9 is a circuit diagram.

Referring first to FIGS. 1 and 2, instrumentation is shown at 10 for sensing differential heating of local body areas or zones. For example, such instrumentation may incorporate a pair of like probes as at 11 and 12 and means thereon to effect heat transfer between the probes and a patient's body zones toward which the probes are respectively applied. In the sketches, the illustrated probes include tips 11a and 12a contacting the skin zones 13 and 14 which run vertically at opposite sides of, and closely straddling, the central spinal column zone 15. The instrumentation includes a carrier in the form of a housing 16' from which the two probes project in extended or deployed positions. As will appear, the probes may also have retracted positions relative to the carrier, one example being seen in FIG. 3, to be described. It is found that differential heating of opposite sections of the zones 13 and 14 occurs at loci of spinal injury, muscle spasm or similar difficulties; that such differential heating can be detected as the probes are run vertically along the zones 13 and 14; and therefore the loci of such zone sections can be determined with accuracy through use of the instrumentation 10. The located sections can then be investigated.

Turning to FIG. 7, a typical probe 11 includes a heat conductive metallic tip 11a having an outer surface shaped for application in heat transfer proximity with a patient's body. The tip may typically have the form of a metallic shell, with a convex outer face 11b, and it consists of a metal selected from the group consisting of silver, brass, copper and stainless steel, for example. Other heat conductive metals may be employed.

Non-metalic material 16 is carried at the inner side of the shell-like tip, such material characterized as electrically insulative and heat conductive. It may advantageously consist, for example, of epoxide resin and shaped in the form of a dome, with a forwardly convex surface 16c matching the concave inner side 11c of the tip, and in intimate heat transfer contact therewith. The rear convex surface 16b of the material faces away from the tip. Both the tip 11a and material 16 are coaxial with respect to central axis 18. Surface 16c is epoxy bonded to the tip.

Electrically energizable means, as for example a thermistor glass bead 17, is centrally supportively embedded in the material 16. The bead is generally coaxial with the tip 11a and material 16, and extends substantially tangentially adjacent the inner concave surface 11c, proximate axis 18, i.e. at 19a. Bead 17 is glass covered.

The means 17 such as the thermistor bead has two electrical leads 20 and 21 which are embedded in the material 16 and project rearwardly therefrom to wrap about the turned terminals of auxiliary or transitional electrical wires 22 and 23, at junctions 24 and 25. The latter may also be soldered. Spaced, relatively heavy wires 22 and 23 pass rearwardly through a central opening 26a in a transverse epoxide header 26 which mounts the rim 11d of the shell-like tip 11a as by an epoxy bond. Note space 27 between the header and material 16 within which the junctions 24 and 25 project. Strain relief is provided in that stressing of the exposed fine leads 20 and 21 is minimized.

Each probe includes a hollow, elongated metallic support 28, as for example a metallic tube. It contains a central cavity 28a containing ambient dead (or non-flowing) air with poor thermal conductivity. Such air contacts the inner exposed side of the tip between the material 16 and rim 11d to inhibit loss of heat in the tip and from that side. Support 28 is joined to the header 26 radially outwardly of the terminals 110a and 111a of heavy wires 110 and 111, insulatively sheathed at 110b and 111b. Strain in wires 110 and 111 is thereby relieved by the header and not passed on to wires 22 and 23, the latter being electrically joined to leads 110 and 111 at junctions 22b and 23b.

The above arrangement results in the tip being heat sensitive in all areas of the shell-like tip. The epoxide header (semi-heat conductive) impedes the transfer of heat to the probe metal tube 28. This allows the tip proper to consist entirely of a good heat conductor, such as one of the above mentioned metals, so that the tip has good heat conductive and transfer sensitivity over its entire dome-like area. This in turn permits scanning of patient's neck regions 115, as seen in FIG. 8, where the side area 116 of the tip, i.e. between material 16 and header 26 contacts the patient's skin. This was not possible in use of the probe described in FIGS. 7 and 8 of my prior U.S. Pat. No. 3,933,149, wherein heat at the side of the probe tip was shorted away from the thermistor bead and into the supporting metal tube.

Also, the relatively thin metal of the shell conducts heat readily toward the bead 17, in FIG. 7, from all regions of the tip 11a, toward zone 19a.

Actuator means is also provided on the carrier and connected with the probes to retract them from active positions (as for example appear in FIGS. 1, 2, 4, 5 and 6) into retracted positions close to the carrier (as for example is seen in FIG. 3). In this regard, the actuator means may for example include manually operable rotors, such as left and right thumb wheels 30 and 31, one for each probe and structure responsive to manual turning of the rotors to displace or return the deployed probes back toward the carrier, and vice versa.

In the example, the carrier may include a forward housing section 16a having a front opening to receive the probes. Worm gears 33 and 34 are pivotally supported at 35, 36 and 36a in the housing section 16a, and are integrally connected, respectively, with the probes 11 and 12 for rotating the probes between extended and retracted positions. For this purpose, the probes may be connected to the worm gears 33 and 34, as shown, and the metal gears may have heat transfer contact or connection with the probe metal shanks to act as heat sinks therefor.

Two worms 37 and 38 are located in the interior 39 of the housing section 16a to mesh with the respective worm gears 33 and 34, the worms typically having a common lateral axis. A central return spring 51 has opposite ends attached to the lateral shaft 38a and to structure 44, so as to yieldably urge the shaft 38a, and worms forwardly into operative engagement with the worm gears. The thumb wheels 30 and 31 are carried by lateral shaft extent 38a between and integral with the worms, so as to rotate the worms 37 and 38 as the thumb wheels are turned. Probe retraction springs (tension springs) 40 and 41 are operatively connected with the probes to yieldably resist rotation of the probes to extended position, i.e. to yieldably maintain the probes in retracted positions, as seen in FIG. 3. One end of each spring is attached to a probe in offset relation to its associated pivot pin, the spring partially wraps about the pin, and the opposite end of the spring attaches to the housing, as shown. The thumb wheels 30 and 31 may be insulated to be thermally isolated from the probes.

Isothermal means is provided on the carrier to be contacted by the probe tips in their retracted positions, so that both tips when stored, are kept at the same temperature. For this purpose, metal clips may be provided at 42 and 43 in the housing interior 39 to be contacted by the retracted probe metal shanks. The clips have interconnection as at 44 to remain at the same temperature. Accordingly, any extraneous thermal condition existing in the probes in use can be purged by simply retracting the probes to contact the clips or "heat sinks".

It should also be noted that the worm end shafts 45 and 46 are received in longitudinal slot bearings 47 and 48 in the housing side walls 49 and 50, respectively. This allows for rearward thumb pressure on the wheels 30 and 31 to disengage the worms from the worm gears which in turn allows the probe return springs to automatically return the probes to the stowed condition. In this manner, the probes may be returned to the stowed position without having to rotate the thumb wheels 30 and 31. If it is desirable not to use the automatic feature the probes can be returned to the stowed condition manually by rotating the wheels 30 and 31 in the opposite direction from that which was used to extend them to the deployed position.

Turning to FIG. 9, the thermistors 17 in the two probes 11 and 12 are incorporated in the legs 60 and 61 of a resistance bridge 100, as indicated, there being other resistors 62 and 63 in leg 64 and resistors 65 and 66 in leg 67. A trimming resistor 68 interconnects legs 64 and 67. Leads 69 and 70 from batteries 71 and 72 connect with the bridge at location 73 and via wiper 74 in sliding contact with trim resistor. Ganged on-off power switches 75 and 76 are provided in series with leads 69 and 70.

A meter 77 is located on the carrier and has one terminal 77a connected with the battery interconnection lead 78. In addition an operational amplifier 79 has inputs 79a and 79b connected with the bridge points 80 and 81 via leads 82 and 83, and the amplifier output 79c is connected with the meter input 77b via zero suppress network 84, and meter current limiting resistor 115 as shown. Various resistors 85 of different ohm rating may be selectively connected in feedback relation across the amplifier by switch 86, to select the operating range desired, i.e. low, medium or high. See switch 86 in FIG. 3, also.

Test switches 90 and 91 are connectible across the resistors 63 and 66, respectively, and gang connected at 92. When both are closed upwardly, as by deflection of switch knob 110 seen in FIG. 3, resistor 63 is shorted, and the meter deflects to one side of zero; and when both are closed downwardly, resistor 66 is shorted, and the meter deflects to the opposite side of zero. The circuitry is "zero'd" by adjustment of wiper 74, with both probes retracted, the on-off switches 75 and 76 being closed.

One useful amplifier 79 is Model LM308 a product of the National Semiconductor Corporation. A useful meter movement is the Parker Meter Movement, a product of Airpax Electronics, Fort Lauderdale, Fla.

Finally, as seen in FIG. 6, the end portion 19a of each support 19 is angled at α about 17 degrees from the probe axis 98 parallel to main surfaces of the receptacle 16, to provide a favorable viewing angle of the instrument visual indicating meter face and instrument controls, while the instrument is in use. Also, in addition to the angle α, the individual probe end portions 19a may be rotated approximately 15 degrees inwards toward one another, in order to maintain relative contact points of tangency when the instrument and the probes are deployed for use in the region of the patient's neck and its attendant surface curvatures.

I claim:

1. In local body heat source sensing instrumentation, the combination comprising
   (a) a probe including a heat conductive, metallic tip having an outer surface shaped for application in heat transfer proximity with a patient's body,
   (b) non-metallic material at the inner side of said tip, said material characterized as electrically insulative and heat conductive, and
   (c) electrically energizable means embedded in said material at a location to detect heat transfer between said surface and source, via said tip and said material,
   (d) the tip having the shape of a shell, with a convex outer surface,
   (e) said means having two electrical leads, there being a heat an electrically insulative header mounting the shell and there being space between said material and the header, and there being auxiliary electrical wires extending through the header and into said space and connected to said leads at locations where the leads project from said material, the header extending transversely crosswise of the shell,
   (f) there being two main wires that terminate at and are supported by the header, said auxiliary wires respectively connected to said two main wires at the side of the header opposite the shell.

2. The combination of claim 1 wherein said tip consists of metal selected from the group consisting of silver, brass, copper and stainless steel.

3. The combination of claim 1 wherein said material consists of an epoxide resin, and said means comprises a thermistor bead.

4. The combination of claim 1 wherein said probe includes a probe tube connected to said header, said auxiliary leads also extending into said tube.

5. The combination of claim 4 wherein the header mounts the shell rim so that said rim and the probe tube are spaced apart by each header.

6. The combination of claim 5 wherein the shell has an annular inner side adjacent said space between the header and said material, the shell having outer surface extent opposite said annular inner side, and which is adapted to contact a patient's neck region.

7. The combination of claim 1 wherein said means comprises a thermistor bead which is generally coaxial with said tip and material, and extends substantially tangentially adjacent the inner surface of said tip.

8. In instrumentation for sensing differential heating of local body areas, the combination comprising,
   (a) a pair of probes, and
   (b) a carrier for the probes, the probes carried by the carrier to have extended and retracted positions relative to the carrier,
   (c) each probe including a heat conductive, metallic tip having an outer surface shaped for application in heat transfer proximity with a patient's body,
   (d) non-metallic material at the inner side of said tip, said material characterized as electrically insulative and heat conductive, and
   (e) electrically energizable means embedded in said material at a location to detect heat transfer between said surface and area, via said tip and said material,
   (f) each tip having hemispherical hollow shell shape, said means comprising a thermistor generally tangential to the interior surface of said shell, said thermistor having two leads, there being a heat and electrically insulative header mounting said shell at the rim thereof and carried by the probe there being space between said material and the header, there being wiring in the probe and associated with the header, and the wiring including auxiliary wires extending through the header into said space and connected with said thermistor leads.

* * * * *